United States Patent
Delaney, Jr. et al.

(10) Patent No.: US 12,297,335 B2
(45) Date of Patent: *May 13, 2025

(54) RADIOPAQUE MULTI-ARMED POLYMERS AND COMPOSITIONS, SYSTEMS AND METHODS PERTAINING TO THE SAME

(71) Applicant: Boston Scientific Scimed Inc., Maple Grove, MN (US)

(72) Inventors: Joseph T. Delaney, Jr., Minneapolis, MN (US); Kolbein K. Kolste, Boxboro, MA (US); Tatyana Dyndikova, Minneapolis, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 446 days.

This patent is subject to a terminal disclaimer.

(21) Appl. No.: 16/999,841

(22) Filed: Aug. 21, 2020

(65) Prior Publication Data
US 2021/0062004 A1 Mar. 4, 2021

Related U.S. Application Data

(60) Provisional application No. 62/892,808, filed on Aug. 28, 2019.

(51) Int. Cl.
| | | |
|---|---|---|
| *C08L 101/00* | (2006.01) | |
| *A61K 49/04* | (2006.01) | |
| *C08G 65/332* | (2006.01) | |
| *C08G 65/333* | (2006.01) | |
| *C08G 65/337* | (2006.01) | |
| *C08J 3/24* | (2006.01) | |
| *C08L 71/02* | (2006.01) | |
| *A61L 27/52* | (2006.01) | |
| *A61L 27/58* | (2006.01) | |
| *C08L 79/02* | (2006.01) | |

(52) U.S. Cl.
CPC .......... *C08L 101/005* (2013.01); *C08J 3/24* (2013.01); *A61L 27/52* (2013.01); *A61L 27/58* (2013.01); *C08L 79/02* (2013.01); *C08L 2201/06* (2013.01); *C08L 2203/02* (2013.01)

(58) Field of Classification Search
CPC .. C08L 101/005; C08L 79/02; C08L 2201/06; C08L 71/02; C08J 3/24; A61K 49/0442; C08G 65/3324; C08G 65/3326; C08G 64/33306; C08G 65/33313; C08G 65/337
See application file for complete search history.

(56) References Cited

U.S. PATENT DOCUMENTS

| | | |
|---|---|---|
| 6,818,018 B1 | 11/2004 | Sawhney |
| 8,383,161 B2 | 2/2013 | Campbell et al. |
| 2007/0248547 A1 | 10/2007 | Brasch et al. |
| 2011/0142936 A1 | 6/2011 | Campbell et al. |
| 2021/0060183 A1* | 3/2021 | Delaney, Jr. ............ C08L 79/02 |

FOREIGN PATENT DOCUMENTS

AU 2009202751 A1 1/2010

OTHER PUBLICATIONS

Chao, M., et al. "The use of TraceIT® as a fiducial marker in bladder radiotherapy." Int J Urol 23 (2016): 47. (Year: 2016).*
Lapienis, Star-shaped polymers having PEO arms, Progress in Polymer Science, vol. 34, Issue 9, 2009, pp. 852-892. (Year: 2009).*
Longmire, Michelle, Peter L. Choyke, and Hisataka Kobayashi. "Dendrimer-based contrast agents for molecular imaging." Current topics in medicinal chemistry 8.14 (2008): 1180-1186. (Year: 2008).*
Fu, Yanjun, et al. "Dendritic iodinated contrast agents with PEG-cores for CT imaging: synthesis and preliminary characterization." Bioconjugate chemistry 17.4 (2006): 1043-1056. (Year: 2006).*
Yordanov, Alexander T., et al. "Novel iodinated dendritic nanoparticles for computed tomography (CT) imaging." Nano Letters 2.6 ( 2002): 595-599. (Year: 2002).*
Sakai, Takamasa, et al. "Design and fabrication of a high-strength hydrogel with ideally homogeneous network structure from tetrahedron-like macromonomers." Macromolecules 41.14 (2008): 5379-5384. (Year: 2008).*
Qiao, Zheng, and Xiangyang Shi. "Dendrimer-based molecular imaging contrast agents." Progress in polymer science 44 (2015): 1-27. (Year: 2016).*
Yue Sun et al., "PGMA-Based Cationic Manoparticles with Polyhydric Iodine Units for Advanced Gene Vectors", BIO Conjugate Chemistry, vol. 27, No. 11, Nov. 16, 2016, pp. 2744-2754.
International Search Report and Written Opinion for the International Patent Application No. PCT/US2020/047439, mailed Oct. 30, 2020, 16 pages.
"Augmenix Announces Positive Three-year SpaceOAR Clinical Trial Results," Imaging Technology News, Oct. 27, 2016.
"Augmenix Receives FDA Clearance to Market its TraceIT™ Tissue Marker," BusinessWire Jan. 28, 2013.

* cited by examiner

*Primary Examiner* — Abigail Vanhorn
(74) *Attorney, Agent, or Firm* — Seager, Tufte & Wickhem, LLP

(57) ABSTRACT

In some aspects, the present disclosure pertains to a polymer that comprises a plurality of polymeric arms, wherein a first portion of the polymeric arms each comprises a reactive end group and wherein a second portion of the polymeric arms each comprises a radiopaque aromatic moiety comprising a monocyclic or multicyclic aromatic structure having a plurality of radiopaque functional groups and a plurality of hydrophilic functional groups. In some aspects, the present disclosure pertains to systems comprising (a) a first composition comprising such a radiopaque polymer and (b) a second composition comprising a multifunctional compound that comprises reactive functional groups that are reactive with the reactive end group. In some aspects, the present disclosure pertains to crosslinked reaction products of (a) such a radiopaque polymer and (b) a multifunctional compound that comprises reactive functional groups that are reactive with the reactive end group.

14 Claims, 3 Drawing Sheets

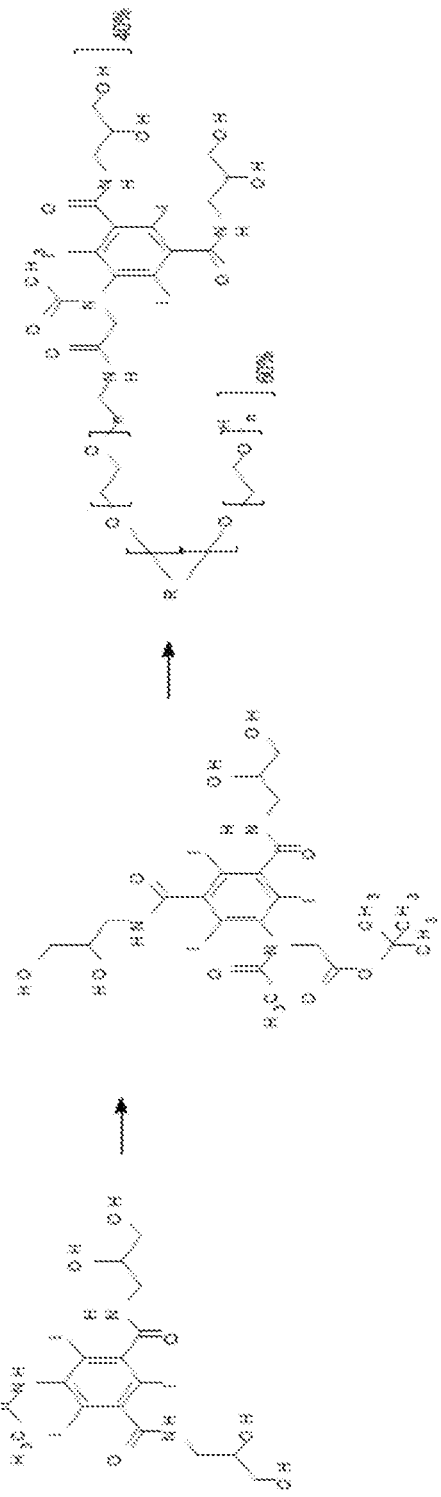
FIG. 2A
FIG. 2B

RADIOPAQUE MULTI-ARMED POLYMERS AND COMPOSITIONS, SYSTEMS AND METHODS PERTAINING TO THE SAME

CROSS-REFERENCE TO RELATED APPLICATION

This application claims the benefit of U.S. Provisional Application No. 62/892,808, entitled "RADIOPAQUE MULTI-ARMED POLYMERS AND COMPOSITIONS, SYSTEMS AND METHODS PERTAINING TO THE SAME" and filed Aug. 28, 2019, the entire disclosure of which is incorporated herein by reference.

FIELD

The present disclosure relates to radiopaque polymers, compositions containing such polymers, methods of making such polymers, and methods of using such polymers, among other aspects. The multi-armed polymers of the present disclosure are useful, for example, in various biomedical applications.

BACKGROUND

Bioerodible injectable hydrogels are a newly emerging class of materials having a variety of medical uses.

As one specific example, in the case of SpaceOAR®, a long-term bioerodible injectable hydrogel based on multi-arm PEG-based, such products are used to create or maintain space between tissues in order to reduce side effects of off-target radiation therapy. See "Augmenix Announces Positive Three-year SpaceOAR® Clinical Trial Results," *Imaging Technology News*, Oct. 27, 2016. As another specific example, Augmenix has developed TraceIT® Hydrogel, a bioerodible injectable hydrogel synthetic hydrogel consisting primarily of water and iodinated cross-linked polyethylene glycol (PEG) that is visible under CT, cone beam, ultrasound and MR imaging and is useful as a tissue marker (e.g., for targeted radiation therapy). See "Augmenix Receives FDA Clearance to Market its TraceIT® Tissue Marker," *BusinessWire* Jan. 28, 2013. TraceIT® hydrogel remains stable and visible in tissue for three months, long enough for radiotherapy, after which it is absorbed and cleared from the body. Id.

Although TraceIT® hydrogel is iodinated as it contains 2,3,5 triiodobenzoate groups, it is not visible on planar x-ray imaging, because the concentration of the 2,3,5 triiodobenzoate groups in the hydrogel is limited by the hydrophobicity of such groups, which can lead to cloudiness in the hydrogel at higher concentrations. Visibility on planar x-ray imaging would enable use as a fiducial marker for state-of-the-art linear accelerators, which use orthogonal co-planar x-ray imaging for continuous localization.

There is a continuing need in the biomedical arts for additional hydrogels, including radiopaque injectable hydrogels having radiopaque moieties in higher concentrations, for precursors of such hydrogels, for methods of making such hydrogels and precursors, for methods of using such hydrogels and precursors, and for systems for forming such hydrogels, among other needs.

SUMMARY

In some aspects, the present disclosure pertains to multi-arm polymers that comprise a plurality of polymeric arms, wherein a first portion of the polymeric arms comprise reactive end groups and wherein a second portion of the polymeric arms comprise radiopaque aromatic moieties that comprise a monocyclic or multicyclic aromatic structure having a plurality of radiopaque functional groups and a plurality of hydrophilic functional groups.

In some embodiments, the monocyclic or multicyclic aromatic structure comprises a benzene group or a naphthalene group.

In some embodiments, which can be used in conjunction with any of the above aspects and embodiments, the plurality of radiopaque functional groups are halide groups.

In some embodiments, which can be used in conjunction with any of the above aspects and embodiments, the plurality of hydrophilic functional groups may be selected from one or more of $C_1$-$C_4$-hydroxyalkyl groups, $C_1$-$C_4$-aminoalkyl groups or $C_1$-$C_4$-carboxyalkyl groups.

In some embodiments, which can be used in conjunction with any of the above aspects and embodiments, the radiopaque aromatic moieties may comprise a 3,5-substituted-2,4,6-triiodobenzene group, wherein a substituent at each of the 3- and 5-positions comprises one of the hydrophilic functional groups and wherein the radiopaque aromatic moiety is linked to a polymeric arm through the 1-position.

In some embodiments, which can be used in conjunction with any of the above aspects and embodiments, the 3,5-substituted-2,4,6-triiodobenzene group may be selected from one or more of a 3,5-hydroxyalkyl-2,4,6-triiodobenzene group, a 3,5-aminoalkyl-2,4,6-triiodobenzene group, or a 3,5-carboxyalkyl-2,4,6-triiodobenzene group.

In some embodiments, which can be used in conjunction with any of the above aspects and embodiments, the radiopaque aromatic moieties may comprise an N,N'-bis(hydroxyalkyl)-2,4,6-triiodobenzene-3,5-dicarboxamide group, an N,N'-bis(aminoalkyl)-2,4,6-triiodobenzene-3,5-dicarboxamide group, or an N,N'-bis(carboxyalkyl)-2,4,6-triiodobenzene-3,5-dicarboxamide group.

In some embodiments, which can be used in conjunction with any of the above aspects and embodiments, the plurality of polymeric arms may be composed of one or more types of hydrophilic monomers.

In some embodiments, which can be used in conjunction with any of the above aspects and embodiments, the plurality of polymeric arms may be composed of one or more monomers selected from N-vinyl pyrrolidone, ethylene oxide, hydroxyethyl acrylate, hydroxyethyl methacrylate, PEG methyl ether acrylate and PEG methyl ether methacrylate.

In some embodiments, which can be used in conjunction with any of the above aspects and embodiments, the plurality of polymeric arms may be attached to a polyol residue core.

In some embodiments, which can be used in conjunction with any of the above aspects and embodiments, the reactive end groups may be selected from one of electrophilic groups and nucleophilic groups.

In some aspects, the present disclosure pertains to systems comprising (a) a first composition comprising a multi-arm polymer in accordance with any of any of the above aspects and embodiments and (b) a second composition comprising a multifunctional compound that comprises reactive functional groups that are reactive with the reactive end groups of the multi-arm polymer.

In some embodiments, the reactive end groups are selected from one of electrophilic groups and nucleophilic groups, and the reactive functional groups are selected from the other of the electrophilic groups and the nucleophilic groups.

In some embodiments, the reactive end groups are electrophilic groups and the functional groups are nucleophilic groups.

In some embodiments, the nucleophilic groups may be amine groups.

In some embodiments, the second composition may comprise a polyamine, for example, a polyamine comprising three or more amine groups.

In some embodiments, which can be used in conjunction with any of the above aspects and embodiments, the system may further comprise a delivery device. For example, the delivery device may comprise a first reservoir containing the first composition and a second reservoir containing the second composition.

In some aspects, the present disclosure pertains to crosslinked reaction products of (a) a multi-arm polymer in accordance with any of the above aspects and embodiments and (b) a multifunctional compound that comprises functional groups that are reactive with the reactive end groups of the multi-arm polymer in accordance with any of the above aspects and embodiments.

BRIEF DESCRIPTION OF THE DRAWINGS

FIGS. 2A-2B schematically illustrate another method of forming a reactive radiopaque multi-armed polymer, in accordance with an embodiment of the present disclosure.

DETAILED DESCRIPTION

Figure 1:
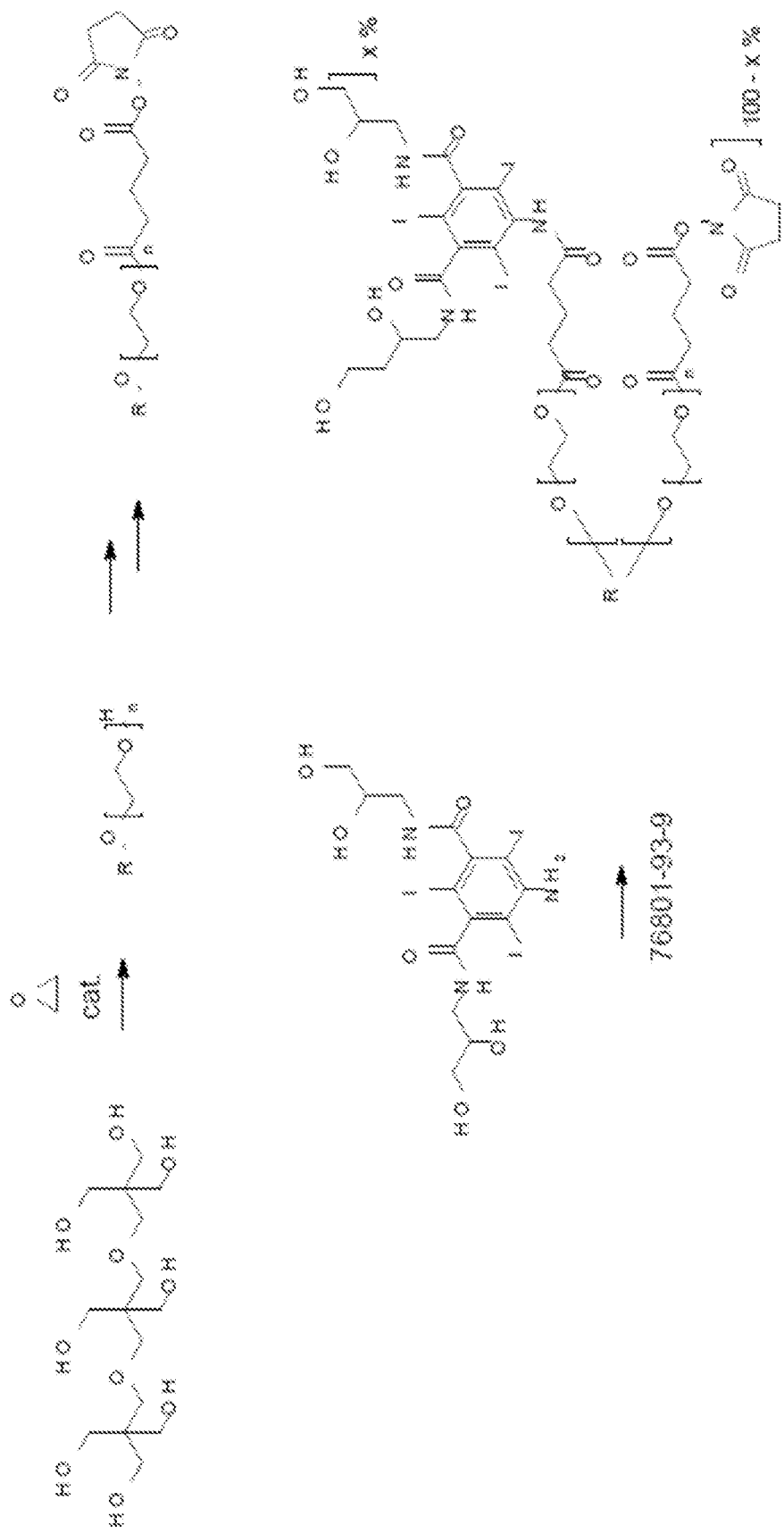
FIG. 1 is a schematic illustration of a method of forming a reactive radiopaque multi-armed polymer, in accordance with an embodiment of the present disclosure.

In various aspects, the present disclosure pertains to radiopaque multi-arm polymers that comprise a plurality of polymeric arms (e.g., having two, three, four, five, six, seven, eight, nine, ten or more arms).

In various embodiments, a first portion of the polymeric arms each comprises a reactive end group and a second portion of the polymeric arms each comprises a radiopaque aromatic moiety that comprise a monocyclic or multicyclic aromatic structure having a plurality of radiopaque functional groups and a plurality of hydrophilic functional groups.

In various embodiments, the polymeric arms are hydrophilic polymeric arms. Such hydrophilic polymeric arms which may be composed of any of a variety of synthetic, natural, or hybrid synthetic-natural polymers including, for example, poly(alkylene oxides) such as poly(ethylene oxide) (also referred to as PEG), poly(propylene oxide) or poly(ethylene oxide-co-propylene oxide), poly(vinylpyrrolidone), poly(vinyl alcohol), poly(allyl alcohol), poly(ethyleneimine), poly(allylamine), poly(vinyl amine), polyoxazolines including poly(2-alkyl-2-oxazolines) such as poly(2-methyl-2-oxazoline), poly(2-ethyl-2-oxazoline) and poly(2-propyl-2-oxazoline), poly(amino acids), polysaccharides, and combinations thereof.

In some embodiments, the polymeric arms extend from a core region. In certain of these embodiments, the core region comprises a residue of a polyol that is used to form the polymeric arms. Illustrative polyols may be selected, for example, from straight-chained, branched and cyclic aliphatic polyols including straight-chained, branched and cyclic polyhydroxyalkanes, straight-chained, branched and cyclic polyhydroxy ethers, including polyhydroxy polyethers, straight-chained, branched and cyclic polyhydroxyalkyl ethers, including polyhydroxyalkyl polyethers, straight-chained, branched and cyclic sugars and sugar alcohols, such as glycerol, mannitol, sorbitol, inositol, xylitol, quebrachitol, threitol, arabitol, erythritol, adonitol, dulcitol, fucose, ribose, arabinose, xylose, lyxose, rhamnose, galactose, glucose, fructose, sorbose, mannose, pyranose, altrose, talose, tagatose, pyranosides, sucrose, lactose, and maltose, oligomers (defined herein as ranging from two to ten units, including dimers, trimers, tetramers, pentamers, hexamers, heptamers, octamers, enneamers and decamers) of straight-chained, branched and cyclic sugars and sugar alcohols, polymers (defined herein as eleven or more units) of straight-chained, branched and cyclic sugars and sugar alcohols, including the preceding sugars and sugar alcohols, starches, amylose, dextrins, cyclodextrins, as well as polyhydroxy crown ethers, and polyhydroxyalkyl crown ethers. Illustrative polyols also include aromatic polyols including 1,1,1-tris(4'-hydroxyphenyl)alkanes, such as 1,1,1-tris(4-hydroxyphenyl)ethane, and 2,6-bis(hydroxyalkyl)cresols, among others. In certain beneficial embodiments, the polyol is an oligomer of a sugar alcohol such as glycerol, mannitol, sorbitol, inositol, xylitol, or erythritol, among others. In certain beneficial embodiments, the polyol may contain three or more hydroxyl groups, for example, between four and twelve hydroxyl groups in certain cases.

In certain embodiments, reactive groups, including reactive end groups, are selected from electrophilic groups and nucleophilic groups.

In certain embodiments, the reactive groups may be nucleophilic groups selected from amine groups and/or thiol groups. In certain embodiments, the reactive groups may be electrophilic groups selected from imidazole esters, imidazole carboxylates, benzotriazole esters, and imide esters, including N-hydroxysuccinimidyl esters. A particularly beneficial reactive group is an N-hydroxysuccinimidyl ester group.

In particular embodiments, a reactive multi-arm polymer may be formed by reacting (a) a polymer that comprises a core (e.g., a polyol residue core, among others) and a plurality of polymeric arms, at least a portion of which are terminated in a hydroxyl group with (b) a cyclic anhydride (e.g., glutaric anhydride, succinic anhydride, malonic anhydride, etc.) to form a reaction product in the form of a polymer that comprises the core and the plurality of polymeric arms, a portion of which are terminated in a moiety that comprises a carboxylic acid group and a hydrolysable ester group positioned between the carboxylic acid group and the polymeric arm. Subsequently, this reaction product may be treated with a coupling agent (e.g., a carbodiimide coupling agent such as N,N'-dicyclohexylcarbodiimide (DCC), 1-Ethyl-3-(3-dimethylaminopropyl)carbodiimide (EDC), N-Hydroxybenzotriazole (HOBt), BOP reagent, and/or another coupling agent) and N-hydroxysuccimide (NHS), to yield a reactive multi-arm polymer comprising succinimidyl end groups, in particular, a reactive multi-arm polymer that comprises a core and a plurality of polymeric arms, a portion of which comprise a moiety that comprises a hydrolysable ester group and a succinimide ester group.

With regard to the aromatic structure that comprises a plurality of radiopaque functional groups and a plurality of hydrophilic functional groups, examples of radiopaque functional groups include halide groups such as iodide groups.

Examples of aromatic structures include those that comprise monocyclic aromatic structures such as those based on benzene and multicyclic aromatic structures such as those based on naphthalene.

Examples of hydrophilic functional groups include hydroxyalkyl groups such as $C_1$-$C_4$-hydroxyalkyl groups (e.g., $C_1$-$C_4$-monohydroxyalkyl groups, $C_1$-$C_4$-dihydroxyalkyl groups, $C_1$-$C_4$-trihydroxyalkyl groups, etc.), $C_1$-$C_4$-aminoalkyl groups (e.g., $C_1$-$C_4$-monoaminoalkyl groups, $C_1$-$C_4$-diaminoalkyl groups, $C_1$-$C_4$-triaminoalkyl groups, etc.), $C_1$-$C_4$-carboxyalkyl groups (e.g., $C_1$-$C_4$-monocarboxyalkyl groups, $C_1$-$C_4$-dicarboxyalkyl groups, $C_1$-$C_4$-tricarboxyalkyl groups, etc.), and combinations thereof.

The hydrophilic functional groups may be linked to the aromatic structures through any suitable linking moiety, which may be selected, for example, from amide groups, amine groups, ether groups, ester groups, or carbonate groups among others.

In certain embodiments, the radiopaque aromatic moiety comprises a 3,5-substituted-2,4,6-trihalobenzene group, wherein a substituent at each of the 3- and 5-positions comprises a hydrophilic functional group selected from those described above, among others, and wherein the radiopaque aromatic moiety is linked to the polymeric arm through the 1-position.

Specific examples may be selected from one or more of a 3,5-hydroxyalkyl-substituted-2,4,6-thiodobenzene group, a 3,5-aminoalkyl-substituted-2,4,6-triiodobenzene group or a 3,5-carboxyalkyl-substituted-2,4,6-thiodobenzene group. As previously indicated, the hydrophilic groups may be linked to the 3 and 5 positions of the benzene ring through any suitable linking moiety, including amide groups, amine groups, ester groups, carbonate groups, or ether groups. For example, in particular embodiments, the linking moiety may be an amide moiety, and the 3,5-substituted-2,4,6-triiodobenzene groups may be selected from N,N'-bis(hydroxyalkyl)-2,4,6-thiodobenzene-3,5-dicarboxamide groups, N,N'-bis(aminoalkyl)-2,4,6-thiodobenzene-3,5-dicarboxamide groups and N,N'-bis(carboxyalkyl)-2,4,6-triiodobenzene-3,5-dicarboxamide groups.

The radiopaque aromatic moiety may in turn be linked to the polymeric arm through a variety of suitable linking moieties including amide groups, amine groups, ester groups, carbonate groups, or ether groups, among others. In certain embodiments, the radiopaque aromatic groups may be linked to the polymeric arm by a linkage that comprises a hydrolytically labile linking moiety, for example, a hydrolytically labile ester group.

In some embodiments, the polymeric arms are formed by polymerization of at least one type of monomer from a suitable multifunctional initiator molecule.

In a particular embodiment, shown schematically in FIG. 1, a cyclic alkylene oxide, specifically, ethylene oxide, is polymerized in the presence of a polyol initiator, specifically, a polyol having eight hydroxyl groups, more specifically, pentaerythritol, and a catalyst, for example, a strong base such as butyl lithium or potassium t-butoxide, to form a polymer in which eight polyalkylene oxide arms extend from a polyol residue core. The terminal hydroxyl groups are then converted to succinimidyl glutarate groups using glutaric anhydride and N-hydroxysuccinimide as reagents. As a next step, the succinimidyl-glutarate-substituted multi-arm polymer is reacted with a 1-amino-3,5-bis(hydroxyalkylaminocarbonyl)-2,4,6-triiodobenzene molecule, specifically, CAS No. 76801-93-9, also referred to herein as 1-amino-3,5-bis(hydroxypropylaminocarbonyl)-2,4,6-triiodobenzene, 1-amino-N,N'-bis(3,5-dihydroxypropyl)-2,4,6-triiodobenzene-1,3-dicarboxamide, or 1-amino-N,N'-bis(3,5-dihydroxypropyl)-2,4,6-triiodoisophthalamide. The relative amount of the 1-amino-3,5-bis(hydroxyalkylaminocarbonyl)-2,4,6-triiodobenzene molecule is adjusted to achieve a stoichiometry wherein a percentage of the succinimidyloxy groups are replaced by amino-3,5-bis(hydroxyalkylaminocarbonyl)-2,4,6-triiodobenzene groups. For example, between 25% and 75% of the succinimidyloxy groups may be replaced in some embodiments.

In an alternative approach, shown schematically in FIGS. 2A-2B, a cyclic alkylene oxide, specifically, ethylene oxide, is polymerized in the presence of a polyol initiator, specifically, a polyol having eight hydroxyl groups, more specifically, pentaerythritol, and a suitable catalyst to form a polymer in which eight polyalkylene oxide arms extend from a polyol residue core. Then, between 25% and 75% of the hydroxyl groups may be replaced by amino groups by reaction with triethylamine and methane sulfonyl chloride in a suitable stoichiometry, followed by addition of an excess of ammonium hydroxide to yield the product shown in FIG. 2A. Turning to FIG. 2B, a 1-alkylamido-3,5-bis(hydroxyalkylaminocarbonyl)-2,4,6-triiodobenzene compound, specifically, Iopromide Related Compound B, CAS 76350-28-2, is treated with t-butyl bromoacetic acid to form an N-(tert-Butoxycarbonyl)-substituted-alkylamido-3,5-bis(hydroxyalkylaminocarbonyl)-2,4,6-triiodobenzene compound. This compound is then reacted with the product of FIG. 2A, such that the amino groups are substituted with carbonylmethylacetamido-3,5-bis(hydroxyalkylaminocarbonyl)-2,4,6-triiodobenzene groups. Subsequently, the adjacent glycolic alcohols are protected as hemiacetals by reaction with 2,2'-dimethoxypropane, then the non-protected —OH groups are allowed to react with glutamic anhydride, followed by deprotection of the hemiacetal, followed by NHS coupling of the carboxylated ester to form the final product.

Using the above and other techniques, reactive radiopaque multi-arm polymers (e.g., one having 2, 3, 4, 5, 6, 7, 8, 9, 10 or more arms) may be formed, which comprise a core and a plurality of polymeric arms extending from the core, wherein a first portion of the polymeric arms each comprises reactive end groups and wherein a second portion of the polymeric arms each comprises a radiopaque aromatic group.

Reactive radiopaque multi-arm polymers formed as described above may be water soluble. Moreover, reactive radiopaque multi-arm polymers formed as described above may be crosslinked with a suitable crosslinking agent, either in vivo or ex vivo, to form a crosslinked hydrogel.

In certain embodiments, the reactive radiopaque multi-arm polymer may be crosslinked with a multifunctional compound having functional groups that are reactive with the reactive groups of the multi-arm polymer. For example, in some embodiments, the reactive groups of the radiopaque multi-arm polymer are nucleophilic groups and the functional groups of the multifunctional compound group are electrophilic groups. In some embodiments, the reactive groups of the reactive radiopaque multi-arm polymer are electrophilic groups and the functional groups of the multifunctional compound are nucleophilic groups. As a specific example, the functional groups of the multifunctional compound may be electrophilic groups selected from imidazole esters, imidazole carboxylates, benzotriazole esters, and imide esters, including N-hydroxysuccinimidyl esters, and the functional groups of the multifunctional compound may be nucleophilic groups selected from amine groups and thiol groups.

In some embodiments, the reactive groups of the reactive radiopaque multi-arm polymer and the functional groups of the multifunctional compound react with one another via an amide coupling reaction.

In various aspects, the present disclosure pertains to a crosslinkable system comprising (a) a first composition comprising a reactive radiopaque multi-arm polymer like that described herein (e.g., a first fluid composition comprising the reactive radiopaque multi-arm polymer or a first dry composition that comprises the radiopaque multi-arm polymer, to which a suitable fluid such as water for injection, saline, etc. can be added to form a fluid composition) and (b) a second composition comprising a multifunctional compound like that described above (e.g., a second fluid composition comprising the multifunctional compound, or a second dry composition that comprises the multifunctional compound, to which a suitable fluid such as water for injection, saline, etc. can be added to form a fluid composition), which comprises functional groups that are reactive with the reactive radiopaque multi-arm polymer. In some embodiments, the reactive groups of the reactive radiopaque multi-arm polymer are electrophilic groups and the functional groups of the multifunctional compound are nucleophilic groups. In some embodiments, the reactive groups of the reactive radiopaque multi-arm polymer and the functional groups of the multifunctional compound react with one another via an amide coupling reaction.

In addition to the reactive radiopaque multi-arm polymer, the first composition may further comprise, for example, therapeutic agents and/or contrast agents, among other possibilities. In addition to the multifunctional compound, the second composition may further comprise, for example, therapeutic agents and/or contrast agents, among other possibilities.

In various embodiments, the system will include one or more delivery devices for delivering the first and second fluid compositions to a subject. For example, the system may include a delivery device that comprises a first reservoir that contains the first fluid composition (or a first dry composition to which a suitable fluid can be added to form the first fluid composition) and a second reservoir that contains the second fluid composition (or a second dry composition to which a suitable fluid such as water for injection, saline, etc. can be added to form the second fluid composition). During operation, the first and second fluid compositions are dispensed from the first and second reservoirs, whereupon the first and second fluid compositions interact and crosslink with one another to form a hydrogel.

In particular embodiments, the system may include a delivery device that comprises a double-barrel syringe, which includes first barrel having a first barrel outlet, which first barrel contains the first composition, a second barrel having a second barrel outlet, which second barrel contains the second composition, a first plunger that is movable in first barrel, and a second plunger that is movable in second barrel.

In some embodiments, the device may further comprise a mixing section having a first mixing section inlet in fluid communication with the first barrel outlet, a second mixing section inlet in fluid communication with the second barrel outlet, and a mixing section outlet. In some embodiments, the device may further comprise a cannula or catheter tube that is configured to receive first and second fluid compositions from the first and second barrels. For example, a cannula or catheter tube may be configured to form a fluid connection with an outlet of a mixing section by attaching the cannula or catheter tube to an outlet of the mixing section, for example, via a suitable fluid connector such as a luer connector.

As another example, the catheter may be a multi-lumen catheter that comprise a first lumen and a second lumen, a proximal end of the first lumen configured to form a fluid connection with the first barrel outlet and a proximal end of the second lumen configured to form a fluid connection with the second barrel outlet. In some embodiments, the multi-lumen catheter may comprise a mixing section having a first mixing section inlet in fluid communication with a distal end of the first lumen, a second mixing section inlet in fluid communication with a distal end of the second lumen, and a mixing section outlet.

During operation, when the first and second plungers are depressed, the first and second fluid compositions are dispensed from the first and second barrels, whereupon the first and second fluid compositions interact and crosslink to form a hydrogel, which is administered onto or into tissue of a subject. For example, the first and second fluid compositions may pass from the first and second barrels, into the mixing section via first and second mixing section inlets, whereupon the first and second fluid compositions are mixed to form an admixture, which admixture exits the mixing section via the mixing section outlet. In some embodiments, a cannula or catheter tube is attached to the mixing section outlet, allowing the admixture to be administered to a subject after passing through the cannula or catheter tube.

As another example, the first fluid composition may pass from the first barrel outlet into the first lumen of a multi-lumen catheter and the second fluid composition may pass from the second barrel outlet into the second lumen of the multi-lumen catheter. In some embodiments the first and second fluid compositions may pass from the first and second lumen into a mixing section at a distal end of the multi-lumen catheter via first and second mixing section inlets, respectively, whereupon the first and second fluid compositions are mixed in the mixing section to form an admixture, which admixture exits the mixing section via the mixing section outlet.

In additional aspects, the present disclosure pertains to crosslinked products of (a) a reactive radiopaque multi-arm polymer as described herein and (b) a multifunctional compound that comprises functional groups that are reactive with the reactive end groups. Such crosslinked products may be formed in vivo (e.g., using a delivery device like that described above), or such crosslinked products may be formed ex vivo and subsequently administered to a subject.

In various embodiments, a reaction product of the functional groups of the multifunctional compound with the reactive end groups of the reactive radiopaque multi-arm polymer are amide linkages.

In certain beneficial embodiments, the reactive groups of the reactive radiopaque multi-arm polymers for use in the first composition of the above systems, and for use in forming the above crosslinked products (i.e., crosslinked products of the reactive radiopaque multi-arm polymers as described herein with the multifunctional compounds as described herein), may be selected from imidazolyl esters, benzotriazole esters, imide esters, including N-hydroxysuccinimidyl esters, and imidazolyl carboxylates, among others.

In certain beneficial embodiments, the multifunctional compound for use in the second composition of the above systems, and for use in forming the above crosslinked products, may be a polyamine. Examples of polyamines suitable for use in the present disclosure include, for example, small molecule polyamines (e.g., containing at least two amine groups, for instance, from 3 to 20 amine groups, in some embodiments), comb polymers having amine side groups, and branched polymers having amine end groups, including dendritic polymers having amine end groups.

Particular examples of multifunctional amines which may be used as the multifunctional compound include trilysine, ethylenetriamine, diethylene triamine, hexamethylenetriamine, di(heptamethylene)triamine, di(trimethylene)triamine, bis(hexamethylene)triamine, triethylene tetramine, tripropylene tetramine, tetraethylene pentamine, hexamethylene heptamine, pentaethylene hexamine, dimethyl octylamine, and dimethyl decylamine, and JEFFAMINE polyetheramines available from Huntsman Corporation, among others. Further particular examples of multifunctional amines include polypeptides including poly(L-lysine), chitosan, and poly(allyl amine), among others.

Figure 3:
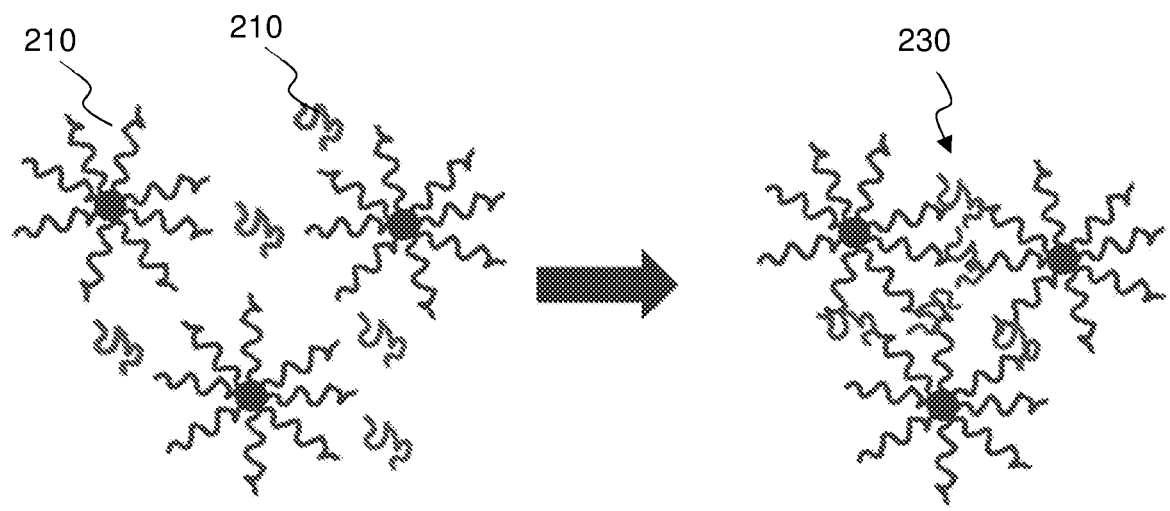
FIG. 3 is a schematic illustration of a method of crosslinking a reactive radiopaque multi-arm polymer with a multifunctional crosslinking agent, in accordance with an embodiment of the present disclosure.

As shown schematically in FIG. 3, a reactive radiopaque multi-arm polymer 210 like that described above (e.g., comprising polymeric arms having reactive succinimidyl-groups) is crosslinked with a multifunctional compound 220 comprising functional groups that are reactive with the reactive groups of the multi-arm polymer 210 (e.g., a polyamine such as trilysine) to form a crosslinked product 230.

Compositions comprising the reactive radiopaque multi-arm polymers described herein, as well as compositions comprising the cross-linked polymers described herein (i.e., crosslinked products of the reactive radiopaque multi-arm polymers described herein with the multifunctional compounds as described herein), can be used in a wide variety of biomedical applications, including medical devices, implants, and pharmaceutical compositions.

In various embodiments, compositions can be formed that include the multi-arm polymers described herein as well as one or more additional agents. In various embodiments, compositions can be formed that include the cross-linked polymers described herein as well as one or more additional agents.

Examples of such additional agents include therapeutic agents, and further imaging agents beyond those present in the multi-arm polymer, among others.

Examples of further imaging agents include (a) fluorescent dyes such as fluorescein, indocyanine green, or fluorescent proteins (e.g. green, blue, cyan fluorescent proteins), (b) contrast agents for use in conjunction with magnetic resonance imaging (MRI), including contrast agents that contain elements that form paramagnetic ions, such as $Gd^{(III)}$, $Mn^{(II)}$, $Fe^{(III)}$ and compounds (including chelates) containing the same, such as gadolinium ion chelated with diethylenetriaminepentaacetic acid, (c) contrast agents for use in conjunction with ultrasound imaging, including organic and inorganic echogenic particles (i.e., particles that result in an increase in the reflected ultrasonic energy) or organic and inorganic echolucent particles (i.e., particles that result in a decrease in the reflected ultrasonic energy), (d) radiocontrast agents, such as those based on the clinically important isotope $^{99m}Tc$, as well as other gamma emitters such as $^{123}I$, $^{125}I$, $^{131}I$, $^{111}In$, $^{57}Co$, $^{153}Sm$, $^{133}Xe$, $^{51}Cr$, $^{81m}Kr$, $^{201}Tl$, $^{67}Ga$, and $^{75}Se$, among others, (e) positron emitters, such as $^{18}F$, $^{11}C$, $^{13}N$, $^{15}O$, and $^{68}Ga$, among others, may be employed to yield functionalized radiotracer coatings, and (f) contrast agents for use in connection with near-infrared (NIR) imaging, which can be selected to impart near-infrared fluorescence to the coatings of the present disclosure, allowing for deep tissue imaging and device marking, for instance, NIR-sensitive nanoparticles such as gold nanoshells, carbon nanotubes (e.g., nanotubes derivatized with hydroxyl or carboxyl groups, for instance, partially oxidized carbon nanotubes), dye-containing nanoparticles, such as dye-doped nanofibers and dye-encapsulating nanoparticles, and semiconductor quantum dots, among others. NIR-sensitive dyes include cyanine dyes, squaraines, phthalocyanines, porphyrin derivatives and borondipyrromethane (BODIPY) analogs, among others.

Compositions in accordance with the present disclosure include lubricious compositions for medical applications, compositions for therapeutic agent release (e.g., by including one or more therapeutic agents in a matrix of the crosslinked polymers, by using the crosslinked polymers to encapsulate one or more therapeutic agents, etc.), and implants (which may be formed ex vivo or in vivo) (e.g., compositions for use as tissue markers, compositions that act as spacers to reduce side effects of off-target radiation therapy, etc.).

What is claimed is:

1. A multi-arm polymer comprising a plurality of polymeric arms that comprise one or more hydrophilic monomers, wherein a first portion of the polymeric arms comprise a reactive imide ester end group comprising a succinimidyl glutarate group and wherein a remaining second portion of the polymeric arms comprise a radiopaque aromatic moiety comprising a monocyclic or multicyclic aromatic structure having a plurality of radiopaque halide groups and a plurality of hydrophilic functional groups that comprise hydrophilic amine groups, the radiopaque aromatic moiety linked to the remaining second portion of the polymer arms through an amide group, wherein the multi-arm polymer is formed by a process wherein between 25% and 75% of the succinimidyl groups of a succinimidyl-glutarate-substituted multi-arm polymer are replaced by radiopaque aromatic moieties.

2. The multi-arm polymer of claim 1, wherein the plurality of radiopaque halide groups are iodine groups.

3. The multi-arm polymer of claim 2, wherein the plurality of hydrophilic functional groups comprise $C_1$-$C_4$-aminoalkyl groups.

4. The multi-arm polymer of claim 1, wherein the monocyclic or multicyclic aromatic structure comprises a benzene group or a naphthalene group.

5. The multi-arm polymer of claim 1, wherein the plurality of hydrophilic functional groups comprise $C_1$-$C_4$-aminoalkyl groups.

6. The multi-arm polymer of claim 1, wherein the radiopaque aromatic moiety comprises a 3,5-substituted-2,4,6-triiodobenzene group, wherein a substituent at each of the 3- and 5-positions comprises one of the hydrophilic functional groups and wherein the radiopaque aromatic moiety is linked to a polymeric arm through the 1-position.

7. The multi-arm polymer of claim 6, wherein the 3,5-substituted-2,4,6-triiodobenzene group is a 3,5-aminoalkyl-2,4,6-triiodobenzene group.

8. The multi-arm polymer of claim 1, wherein the radiopaque aromatic moiety comprises an N,N'-bis(aminoalkyl)-2,4,6-triiodobenzene-3,5-dicarboxamide group.

9. The multi-arm polymer of claim 1, wherein the one or more hydrophilic monomers are selected from ethylene oxide, hydroxyethyl acrylate, and hydroxyethyl methacrylate.

10. The multi-arm polymer of claim 1, wherein the plurality of polymeric arms are attached to a polyol residue core.

11. A system comprising (a) a first composition comprising the multi-arm polymer of claim 1 and (b) a second composition comprising a multifunctional amine compound that comprises reactive amine functional groups that are reactive with the reactive imide ester end group.

12. The system of claim 11, further comprising a delivery device.

13. The system of claim 12, wherein the delivery device comprises a first reservoir containing the first composition and a second reservoir containing the second composition.

14. A crosslinked reaction product of (a) the multi-arm polymer of claim 1 and (b) a multifunctional amine compound that comprises amine reactive functional groups that are reactive with the reactive reactive imide ester end group.

* * * * *